(12) United States Patent
Kanada (10) Patent No.: US 9,852,529 B2
(45) Date of Patent: Dec. 26, 2017

(54) GRAPH DISPLAY APPARATUS, ITS OPERATION METHOD AND NON-TRANSITORY COMPUTER-READABLE RECORDING MEDIUM HAVING STORED THEREIN GRAPH DISPLAY PROGRAM

(71) Applicant: FUJIFILM Corporation, Tokyo (JP)

(72) Inventor: Shoji Kanada, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 185 days.

(21) Appl. No.: 14/864,889

(22) Filed: Sep. 25, 2015

(65) Prior Publication Data

US 2016/0012621 A1 Jan. 14, 2016

Related U.S. Application Data

(63) Continuation of application No. PCT/JP2014/001765, filed on Mar. 27, 2014.

(30) Foreign Application Priority Data

Mar. 29, 2013 (JP) ................................ 2013-071422

(51) Int. Cl.
*G06T 11/20* (2006.01)
*G06F 3/048* (2013.01)
(Continued)

(52) U.S. Cl.
CPC ............ *G06T 11/206* (2013.01); *G06F 3/048* (2013.01); *G06F 19/321* (2013.01);
(Continued)

(58) Field of Classification Search
None
See application file for complete search history.

(56) References Cited

U.S. PATENT DOCUMENTS 6,356,256 B1 * 3/2002 Leftwich ............... G06F 3/0481
345/1.1
6,704,012 B1 * 3/2004 Lefave .................. G06T 11/206
345/440

(Continued)

FOREIGN PATENT DOCUMENTS

| JP | H03138522 | 6/1991 |
| JP | H0683880 | 3/1994 |

(Continued)

OTHER PUBLICATIONS

H. Okamura, "Excel o Tsukai Konasu Internet Setsuzokuryo (2)", Nikkei Personal Computing, No. 380, Mar. 5, 2001, pp. 293-297, Japan.

(Continued)

*Primary Examiner* — Frank Chen
(74) *Attorney, Agent, or Firm* — JCIPRNET (57) ABSTRACT

When line graphs are displayed on coordinates having a horizontal axis as a time axis and a vertical axis as an axis representing examination values, the number of pieces of examination data having probabilities of presence in a display period of the time axis is obtained by comparing a standard examination interval, which is a standard interval at which examination of each of the plurality of examination items is performed, and the display period. An ordinary display mode or a low visual recognizability display mode, in which visual recognizability is low, is determined, based on whether the obtained number of pieces of examination data is greater than or equal to a threshold, as a display mode of a line graph for each of the examinations. Plural line graphs overlapping with each other are displayed on the coordinates in each display mode.

10 Claims, 6 Drawing Sheets

(51) Int. Cl.
*G06Q 50/24* (2012.01)
*G06Q 10/06* (2012.01)
*G06Q 10/10* (2012.01)
*G06F 19/00* (2011.01)

(52) U.S. Cl.
CPC . *G06Q 10/063114* (2013.01); *G06Q 10/1091* (2013.01); *G06Q 50/24* (2013.01)

(56) References Cited

U.S. PATENT DOCUMENTS

| | | | |
|---|---|---|---|
| 2005/0010447 A1 | 1/2005 | Miyasaka et al. | |
| 2011/0074788 A1* | 3/2011 | Regan | G06F 19/3406 345/440 |
| 2013/0070286 A1* | 3/2013 | Gross | H04N 1/00949 358/1.15 |
| 2014/0022256 A1* | 1/2014 | Carnes | G06T 11/206 345/440.1 |
| 2014/0068490 A1* | 3/2014 | Ayers | G06F 17/30554 715/771 |

FOREIGN PATENT DOCUMENTS

| | | |
|---|---|---|
| JP | H0991316 | 4/1997 |
| JP | 2005301816 | 10/2005 |
| WO | 03005265 | 1/2003 |

OTHER PUBLICATIONS

H. Tsutsuki, "Rikei no Tameno Windows 3", PC Wave, Aug. 1, 1995, pp. 124-130, vol. 3, No. 8, Japan.
"International Search Opinion (FormPCT/ISA/237)", dated Jul. 29, 2014, with partial English translation thereof, pp. 1-4.

* cited by examiner

GRAPH DISPLAY APPARATUS, ITS OPERATION METHOD AND NON-TRANSITORY COMPUTER-READABLE RECORDING MEDIUM HAVING STORED THEREIN GRAPH DISPLAY PROGRAM

CROSS-REFERENCE TO RELATED APPLICATIONS

This application is a Continuation of PCT International Application No. PCT/JP2014/001765 filed on Mar. 27, 2014, which claims priority under 35 U.S.C. §119(a) to Japanese Patent Application No. 2013-071422 filed on Mar. 29, 2013. Each of the above applications is hereby expressly incorporated by reference, in its entirety, into the present application.

BACKGROUND

The present disclosure relates to a graph display apparatus for displaying examination results of plural examinations performed on a patient by line graphs, an operation method of the graph display apparatus, and a graph display program.

In medical fields of recent years, when diagnosis is performed on a patient, plural results of examinations performed on the patient are displayed and used as reference information for diagnosing a disease name, deciding a treatment policy or the like.

There are many kinds of examination performed on patients. In actual clinical scenes, when a patient is suspected of a specific disease, a doctor performs diagnosis or treatment by referring to each examination result of plural examinations that are considered to be important to diagnose the specific disease. However, it is difficult to display all the results of examinations performed on the patient because the size of a display is limited. Further, if too much information is displayed on a display screen, that will become even a negative factor as observation becomes rather difficult.

In conventional systems, an operator selected important results or results in which he/she had interest from results obtained by examinations, and the results were displayed by graphs. Further, items to be displayed together with the graphs were selected by the operator from many items of treatment performed on the patient (medication and injection). Therefore, some methods were proposed to reduce the work of operators. In the methods, conditions for displaying the content of treatment and a change in examination results were determined by managing items to be displayed by graphs, display modes and the like for each disease (for example, Japanese Unexamined Patent Publication No. 6(1994)-083880 (Patent Document 1)).

SUMMARY

Each disease has necessary examination items. However, even if a patient has the same disease, vital examinations must be performed many times every day while the patient is hospitalized, and a short-term course of the condition of the patient must be recognized. Meanwhile, some other examinations are performed every few days or every few months. An interval of examination is different in this manner, depending on examination, and changes in all of such examinations need to be recognized. Therefore, a tendency is checked in a display period appropriate for checking the result of each examination by switching display periods of graphs based on an examination to be checked. Especially, in circulatory diseases and diseases of kidneys, many examination results must be checked to make judgments, and too many graphs are displayed.

Further, when a long-term course of the condition of a patient is observed, if graphs of vital data including many pieces of examination data are present, there is a problem that it becomes difficult to observe examination data for observing the long-term course because of the presence of vital data. Meanwhile, display in a part of a display period is enlarged to check vital data, which change in a short term period, but only lines are displayed in graphs of examination data obtained by examination at long. time intervals. Therefore, there is a problem that it is difficult to observe examination data for observing the long-term course.

In the method of Patent Document 1, conditions for displaying the content of treatment and a change in examination data were determined by managing items to be displayed by graphs, display modes and the like for each disease. However, when both of a graph of examination data including many pieces of examination data for observing a short term course and a graph of examination data at a long examination interval for observing a long-term course were present, it was impossible to prevent observation of the graphs from becoming difficult.

In view of the foregoing circumstances, the present disclosure provides a graph display apparatus that generates graphs representing changes of examination data in plural examinations in such a manner that the changes of examination data in the plural examinations are recognizable, an operation method of the graph display apparatus, and a graph display program.

A graph display apparatus of the present disclosure displays, on coordinates having a horizontal axis and a vertical axis, one of which is a time axis and the other one is an axis of examination values, line graphs connecting data points representing examination data about a patient by lines in order of time of examination for plural examination items. The graph display apparatus includes a display mode determination means that obtains the number of pieces of examination data having probabilities of presence in a display period of the time axis by comparing a standard examination interval, which is a standard interval at which examination of each of the plural examination items is performed, and the display period, and determines, based on whether the obtained number of pieces of examination data is greater than or equal to a threshold, an ordinary display mode or a low visual recognizability display mode, in which visual recognizability is low, as a display mode of a line graph for each of the plural examination items, and a graph display means that generates the line graphs of examination data for the plural examination items according to the display mode that has been determined for each of the plural examination items, and displays the line graphs on the coordinates.

An operation method of a graph display apparatus of the present disclosure is an operation method of the graph display apparatus that displays, on coordinates having a horizontal axis and a vertical axis, one of which is a time axis and the other one is an axis of examination values, line graphs connecting data points representing examination data about a patient by lines in order of time of examination for plural examination items. The operation method includes a display mode determination step in which a display mode determination means obtains the number of pieces of examination data having probabilities of presence in a display period of the time axis by comparing a standard examination interval, which is a standard interval at which examination of each of the plural examination items is performed, and the display period, and determines, based on whether the obtained number of pieces of examination data is greater than or equal to a threshold, an ordinary display mode or a low visual recognizability display mode, in which visual recognizability is low, as a display mode of a line graph for each of the plural examination items, and a graph display step in which a graph display means generates the line graphs of examination data for the plural examination items according to the display mode that has been determined for each of the plural examination items, and displays the line graphs on the coordinates.

A graph display program of the present disclosure causes a computer of a graph display apparatus that displays, on coordinates having a horizontal axis and a vertical axis, one of which is a time axis and the other one is an axis of examination values, line graphs connecting data points representing examination data about a patient by lines in order of time of examination for plural examination items to function as a display mode determination means that obtains the number of pieces of examination data having probabilities of presence in a display period of the time axis by comparing a standard examination interval, which is a standard interval at which examination of each of the plural examination items is performed, and the display period, and determines, based on whether the obtained number of pieces of examination data is greater than or equal to a threshold, an ordinary display mode or a low visual recognizability display mode, in which visual recognizability is low, as a display mode of a line graph for each of the plural examination items, and a graph display means that generates the line graphs of examination data for the plural examination items according to the display mode that has been determined for each of the plural examination items, and displays the line graphs on the coordinates.

Each examination of an "examination item" obtains a piece of examination data. The "number of pieces of examination data" means the number of times of performed examination. The "number of pieces of examination data having probabilities of presence in a display period" means the number of pieces of examination data having probabilities that they were obtained by performing examination in the display period, and the number may be different from the number of times of examination actually performed in some cases.

Further, the "low visual recognizability display mode, in which visual recognizability is low" means a display mode in which it is difficult to visually recognize data, compared with an ordinary display mode. The "low visual recognizability display mode" includes a simple display mode, in which simpler display than an ordinary display mode is performed, and non-display. Further, the expression "determines an ordinary display mode or a low visual recognizability display mode, in which visual recognizability is low, as a display mode" refers to cases including a case in which an ordinary display mode or a simple display mode is determined as the display mode, and a case in which an ordinary display mode or non-display is determined as the display mode. Further, the simple display mode is, for example, a mode in which a part of elements constituting a line graph in an ordinary display mode, such as the color of a line and a mark, is omitted or varied.

The display mode determination means may compare the display period and the standard examination interval of each of the plural examination items, and determine the ordinary display mode, as the display mode of a line graph for an examination item in which the number of pieces of examination data having probabilities of presence in the display period is less than or equal to a first threshold, and determine the low visual recognizability display mode, as the display mode of a line graph for an examination item in which the number of pieces of examination data having probabilities of presence in the display period is greater than the first threshold.

The display mode determination means may compare the display period and the standard examination interval of each of the plural examination items, and determine the ordinary display mode, as the display mode of a line graph for an examination item in which the number of pieces of examination data having probabilities of presence in the display period has been judged to be greater than or equal to a second threshold, and determine the low visual recognizability display mode, as the display mode of a line graph for an examination item in which the number of pieces of examination data having probabilities of presence in the display period has been judged to be less than the second threshold.

It is desirable that a display period switching receipt means that receives switching to display in which display in a part of the display period is enlarged is further provided. It is desirable that when switching to the display has been received, the display mode determination means compares the part of the display period and the standard examination interval of each of the plural examination items, and determines the ordinary display mode, as the display mode of a line graph for an examination item in which the number of pieces of examination data having probabilities of presence in the part of the display period has been judged to be greater than or equal to a second threshold, and determines the low visual recognizability display mode, as the display mode of a line graph for an examination item in which the number of pieces of examination data having probabilities of presence in the part of the display period has been judged to be less than the second threshold.

It is desirable that a standard examination interval determination means is further provided. The standard examination interval determination means obtains, for each of the plurality of examination items, examination intervals between examinations performed on a plurality of patients, and determines a predetermined examination interval among examination intervals within a predetermined range from an average or a median of the examination intervals at which examination for each of the plurality of examination items has been performed, as the standard examination interval.

The standard examination interval may be determined based on a disease.

When the line graph displayed in the ordinary display mode connects data points representing examination data, the line graph displayed in the low visual recognizability display mode may be a line graph in which data points representing examination data are not connected, but only a mark indicating a position of each of the data points representing examination data is displayed.

Further, when the line graph displayed in the ordinary display mode connects data points representing examination data and also displays a mark indicating a position of each of the data points, the line graph displayed in the low visual recognizability display mode may be a line graph in which no mark indicating a position of each of the data points is displayed, but data points representing examination data are only connected.

According to the present disclosure, when line graphs connecting data points representing examination data by lines in order of time of examination for plural examination items are generated, the number of pieces of examination data having probabilities of presence in a display period of the time axis is obtained by comparing a standard examination interval, which is a standard interval at which examination of each of the plural examination items is performed, and the display period, and a line graph for each of the plural examination items is displayed in an ordinary display mode or a low visual recognizability display mode, in which visual recognizability is low, based on whether the obtained number of pieces of examination data is greater than or equal to a threshold. Therefore, it is possible to observe, based on whether a change in examination data obtained at a short interval needs to be observed or a change in examination data obtained at a long time interval needs to be observed, only a change in which a user has an interest.

Further, the ordinary display mode may be determined as the display mode of a line graph for an examination item in which the number of pieces of examination data having probabilities of presence in a display period has been judged to be less than or equal to a first threshold, and the low visual recognizability display mode may be determined as the display mode of a line graph for an examination item in which the number of pieces of examination data having probabilities of presence in the display period has been judged to be greater than the first threshold. Then, a line graph for an examination item at a long examination interval, in which pieces of examination data the number of which is only less than or equal to the first threshold are present, becomes easily observable.

Alternatively, the ordinary display mode may be determined as the display mode of a line graph for an examination item in which the number of pieces of examination data having probabilities of presence in a display period has been judged to be greater than or equal to a second threshold, and the low visual recognizability display mode may be determined as the display mode of a line graph for an examination item in which the number of pieces of examination data having probabilities of presence in the display period has been judged to be less than the second threshold. Then, a line graph for an examination item at a short examination interval, in which pieces of examination data the number of which is greater than or equal to the second threshold are present, becomes easily observable.

Further, statistics of time intervals at which each examination was performed on plural patients may be collected, and a predetermined examination interval among examination intervals in a predetermined range from an average or a median of the examination intervals may be determined, as a standard examination interval. Then, it is possible to determine a display mode according to an examination interval at which each examination is performed.

Further, a standard examination interval may be determined for each disease instead of each examination item. Then, it is possible to achieve a most appropriate display mode in which a difference in the characteristics of diseases is taken into consideration.

Further, a line graph displayed in a low visual recognizability display mode may be a line graph in which data points representing examination data are not connected, but only a mark indicating a position of each of the data points representing examination data is displayed, or a line graph in which no mark indicating a position of each of the data points is displayed, but data points representing examination data are only connected. Then, it is possible to prevent interference with observation of a line graph to be observed.

DESCRIPTION OF THE PREFERRED EMBODIMENTS

Figure 1:
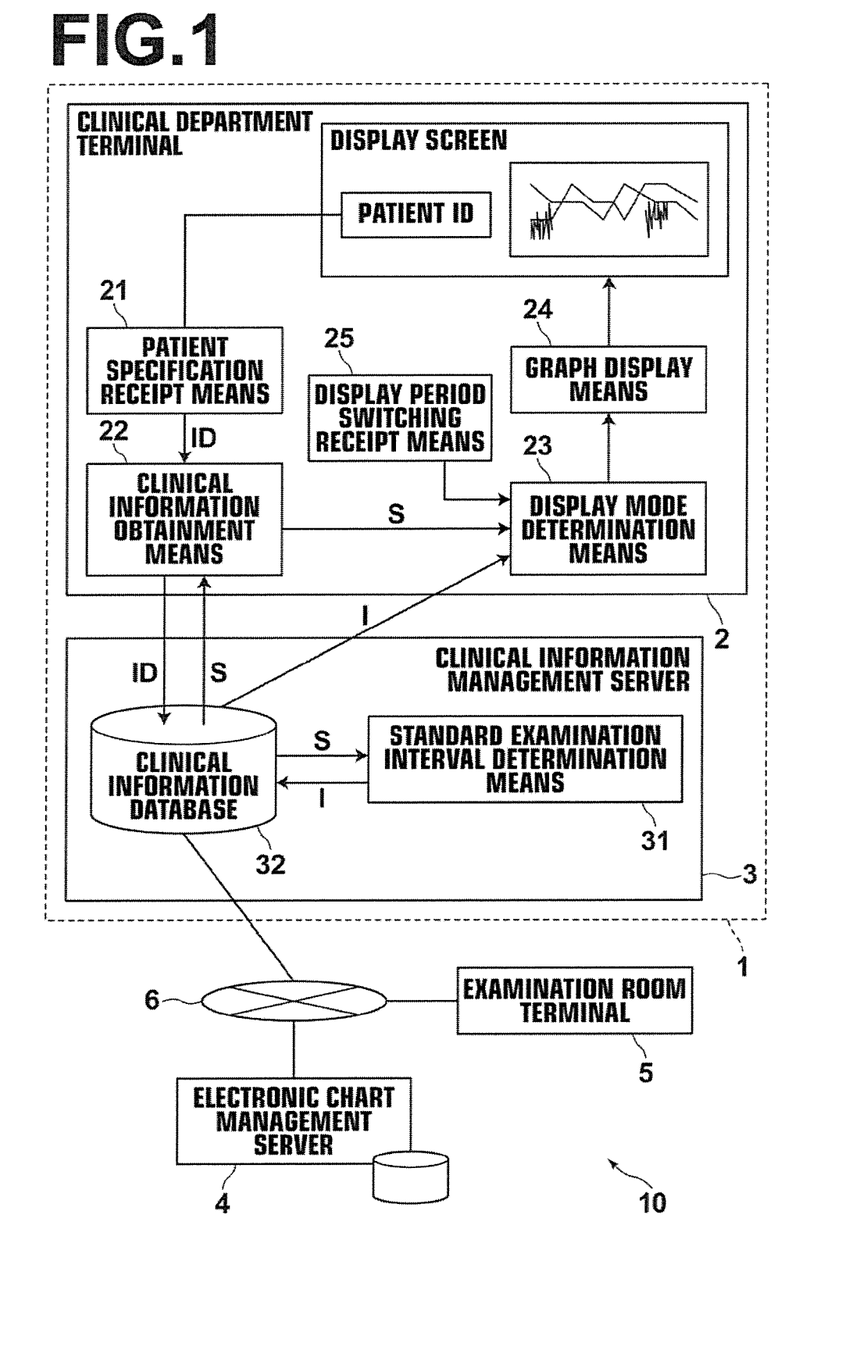
FIG. 1 is a schematic diagram illustrating the configuration of a clinical information system to which a graph display apparatus according to an embodiment of the present disclosure has been applied.

Hereinafter, embodiments of a graph display apparatus of the present disclosure will be described with reference to FIG. 1. FIG. 1 is a schematic diagram illustrating the configuration of a clinical information system to which a graph display apparatus according to an embodiment of the present disclosure has been applied.

As illustrated in FIG. 1, a clinical information system 10 includes a clinical department terminal 2, a clinical information management server 3, an electronic chart management server 4, an examination room terminal 5 and a network 6.

The electronic chart management server 4 is a computer including an electronic chart database in which electronic charts are stored. An operating system and software for managing the database have been installed in the electronic chart management server 4. Further, software for retrieving, based on a request by the clinical department terminal 2 or the like, clinical information S, such as examination data, related to each electronic chart, and sending and receiving a retrieval result has been installed in the electronic chart management server 4. The electronic chart management server 4 is connected to the clinical information management server 3, the clinical department terminal 2, the examination room terminal 5 and the like through the network 6 in such a manner that each clinical information managed in an electronic chart is obtainable.

The examination room terminal 5 is a computer installed in an examination room that is separate from each clinical department. The examination room terminal 5 is used to input information about examination data of examination performed in the examination room based on an examination order that has been input at each clinical department terminal 2. Standard software, such as an operating system, has been installed in the examination room terminal 5. Further, software for retrieving an examination order and inputting examination data has been installed in the examination room terminal 5. Information about examination data of examination performed in each examination room is input at the examination room terminal 5 in such a manner to be related to an examination order or a patient ID. Further, the clinical information management server 3, which will be described later, functions also as a server for managing information about examination data that have been input at the examination room terminal 5. The information about the input examination data is also stored, as clinical information S, in the clinical information database 32.

In the embodiment of the present disclosure, the graph display apparatus 1 includes the clinical information management server 3 and the clinical department terminal 2. Each of computers of the clinical information management server 3 and the clinical department terminal 2 is controlled by a graph display program installed from a recording medium, such as a CD-ROM, and functions as the graph display apparatus 1 in the embodiment of the present disclosure. The graph display program may be installed after being downloaded from a storage unit of a server connected through a network, such as the Internet. In FIG. 1, the clinical information management server 3 and the clinical department terminal 2 are directly connected to each other. Alternatively, the clinical information management server 3 and the clinical department terminal 2 may be connected to each other through the network 6.

The clinical information management server 3 is a computer including a clinical information database 32. The clinical information management server 3 is connected to the electronic chart management server 4, the examination room terminal 5 and the like through the network 6. The clinical information management server 3 obtains clinical information S, such as an electronic chart of a patient and various kinds of examination data, by retrieving it, based on the patient ID of the patient, from each connected server or the like. Further, the clinical information management server 3 stores clinical information S in such a manner to be related to each patient ID. When a patient has plural diseases, the clinical information management server 3 stores clinical information S related to the patient ID by classifying clinical information S for the plural diseases. The clinical information management server 3 updates clinical information S to be managed at fixed time every day.

An operating system and software for managing a database have been installed in the clinical information management server 3. Further, a program related to processing for determining a standard examination interval in the graph display program according the embodiment of the present disclosure has been installed in the clinical information management server 3. In the graph display program according the embodiment of the present disclosure has been installed in the clinical information management server 3. When this program is executed, the clinical information management server 3 functions as standard examination interval determination means 31 that determines a standard examination interval for each examination with respect to plural examinations for diagnosis or diagnosis and treatment.

The clinical department terminal 2 is a computer used by a doctor of a clinical department or the like to retrieve clinical information S about a patient, to input an examination order or the like. The clinical department terminal 2 includes a display device, which is a general display, and an input device including a keyboard, a mouse and the like. Further, the clinical department terminal 2 is used also to display and refer to a graph representing a change in examination data of performed examination, and clinical information S, such as a generated electronic chart. Standard software, such as an operating system, and application software, such as a clinical information integrated display viewer for displaying clinical information S, such as a generated electronic chart, have been installed in the clinical department terminal 2.

Parts defining patient specification receipt processing, clinical information obtainment processing, display mode determination processing, graph display processing and display period switching receipt processing in the graph display program according to the embodiment of the present disclosure have been installed in the clinical information integrated viewer. When this graph display program is executed, the clinical department terminal 2 functions as the patient specification receipt means 21, the clinical information obtainment means 22, the display mode determination means 23, the graph display means 24 and the display period switching receipt means 25.

Further, graph generation information necessary to generate a time series graph for each disease has been set, in advance, in the clinical information integrated display viewer. The graph generation information includes a disease name, examination items of examination to be represented by graphs, a display range of a vertical axis of graphs, a display range (display period) of a horizontal axis of the graphs, colors, line types, marks, fonts and font sizes, which are necessary to generate graphs. Here, the examination items represented by the graphs are plural examination items set in advance according to a disease, and which are considered to be important to diagnose the disease. Further, the display range of the vertical axis of the graph has been set based on possible values of examination data for each examination corresponding to an examination item. The display range of the horizontal axis of the graph in the graph generation information is determined after obtainment of clinical information S about each patient in such a manner that the display range coincides with a time period in which examination data about each patient are present. However, values other than the display range of the horizontal axis in the graph generation information have been set in advance.

Figure 2A:
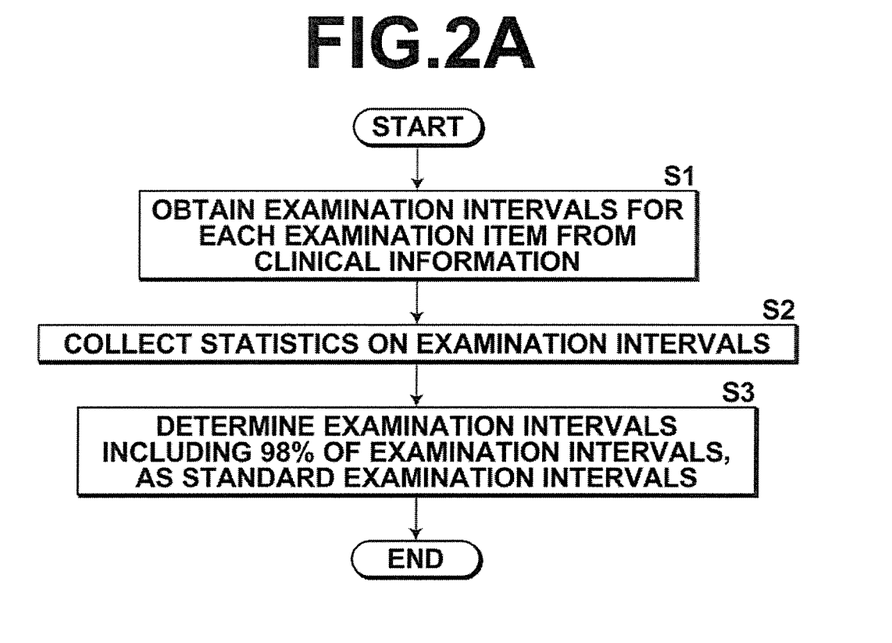
FIG. 2A is a flow chart showing a flow of processing for determining a standard examination interval.
Figure 2B:
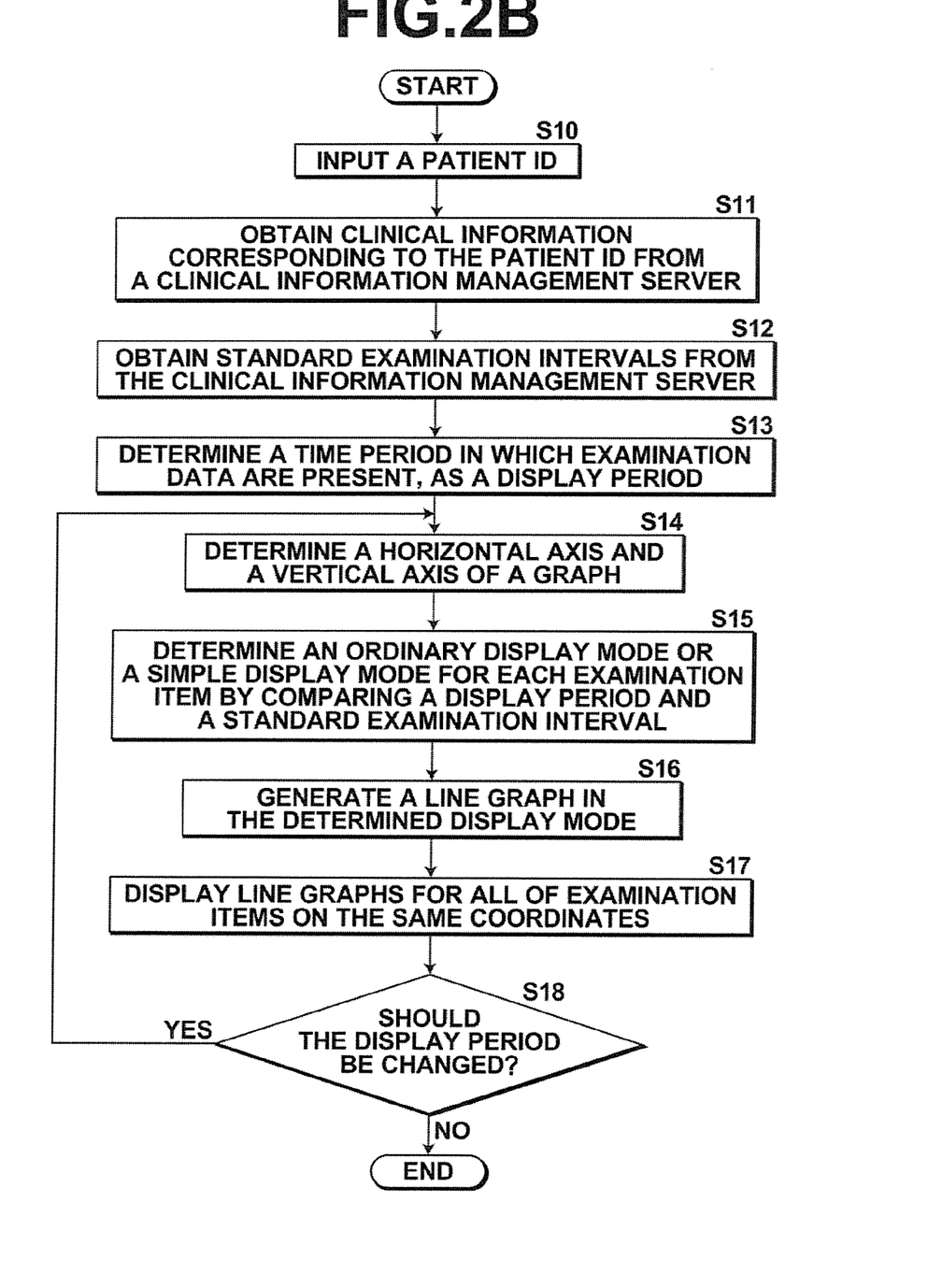
FIG. 2B is a flow chart showing a flow of processing for displaying graphs at a clinical department terminal.

FIG. 2A, FIG. 2B are flow charts showing a flow of processing at a graph generation apparatus. A flow of processing in the graph generation apparatus will be described with reference to FIG. 2A and FIG. 2B.

First, a flow of processing for determining a standard examination interval in the clinical information management server 3 will be described with reference to FIG. 1 and FIG. 2A.

The standard examination interval determination means 31 obtains examination intervals at which examination Ti ($1<i\leq n$: n is the number of kinds of examination) for examination item i was performed from plural pieces of clinical information S stored in the clinical information database 32 (S1). A frequency distribution of examination intervals of examination Ti is generated based on obtained plural examination intervals of examination Ti (S2). Here, when an examination interval is long, such as one year or longer, a probability that a patient was not regularly seeing a doctor in the time period is high. Therefore, the time interval is excluded from statistics. Examination intervals that include 98% of examination intervals at which examination Ti was performed may be considered, as standard examination intervals. Therefore, examination intervals to which 98% of the examination intervals belong are set as standard examination intervals I (S3). Standard examination intervals I for each examination item i are stored in the clinical information database 32. Here, a range including 98% of examination intervals is regarded as the range of standard examination intervals. An appropriate threshold should be determined so that an interval that is not an ordinary interval of examination Ti is excluded from examination intervals of examination Ti.

Figure 3:
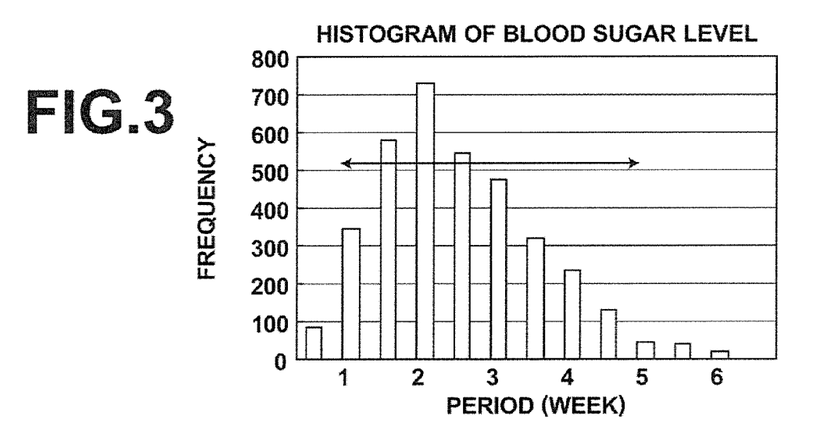
FIG. 3 is a frequency distribution histogram of white blood sugar level.
Figure 4:
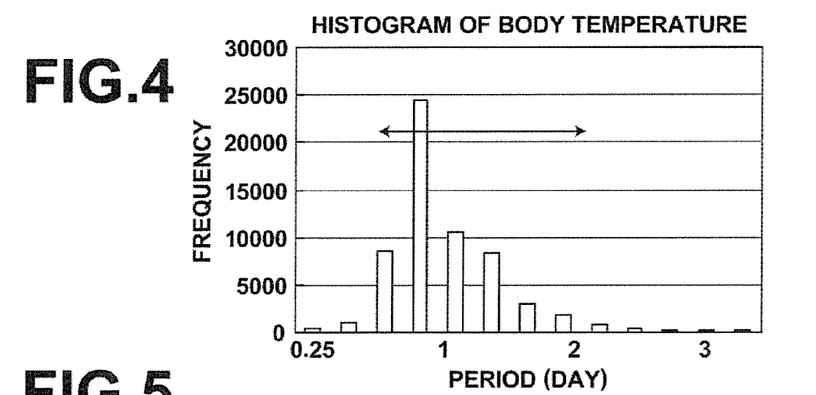
FIG. 4 is a frequency distribution histogram of body temperature.

Specific methods for calculating standard examination intervals I for each examination of body temperature and blood sugar level by using cumulative frequencies will be described by using the examples shown in Table 1 and Table 2. Table 1 shows the numbers of times (frequencies) of extraction of examination intervals for blood sugar level, relative frequencies and cumulative relative frequencies. FIG. 3 is a frequency distribution histogram corresponding to Table 1. Table 2 shows the numbers of times (frequencies) of extraction of examination intervals for body temperature, relative frequencies and cumulative relative frequencies. FIG. 4 is a frequency distribution histogram corresponding to Table 2. In Table 1 and Table 2, a shadow part indicates intervals including 98% of examination data. These intervals are ranges in which an average or a median of examination data is always included. In FIGS. 3 and 4, a range indicated by an arrow is a 98% interval.

TABLE 1

EXAMPLE OF BLOOD SUGAR LEVEL

| PERIOD (WEEK) | FREQUENCY | RELATIVE FREQUENCY | CUMULATIVE RELATIVE FREQUENCY |
|---|---|---|---|
| 0.5 | 83 | 0.023 | 0.023 |
| 1 | 347 | 0.098 | 0.121 |
| 1.5 | 582 | 0.164 | 0.285 |
| 2 | 731 | 0.206 | 0.491 |
| 2.5 | 546 | 0.154 | 0.645 |
| 3 | 475 | 0.134 | 0.779 |
| 3.5 | 319 | 0.09 | 0.868 |
| 4 | 234 | 0.066 | 0.934 |
| 4.5 | 129 | 0.036 | 0.971 |
| 5 | 43 | 0.012 | 0.983 |
| 5.5 | 39 | 0.011 | 0.994 |
| 6 | 20 | 0.006 | 0.999 |
| 6.5 | 2 | 0.001 | 1 |
| TOTAL | 3550 | | |

STATISTICAL MAXIMUM TIME PERIOD: 5 WEEKS
STATISTICAL MINIMUM TIME PERIOD: 1 WEEK

TABLE 2

EXAMPLE OF BODY TEMPERATURE

| PERIOD (DAY) | FREQUENCY | RELATIVE FREQUENCY | CUMULATIVE RELATIVE FREQUENCY |
|---|---|---|---|
| 0.25 | 483 | 0.008 | 0.008 |
| 0.5 | 925 | 0.015 | 0.023 |
| 0.75 | 8640 | 0.144 | 0.168 |
| 1 | 24357 | 0.406 | 0.574 |
| 1.25 | 10509 | 0.175 | 0.749 |
| 1.5 | 8286 | 0.138 | 0.888 |
| 1.75 | 3032 | 0.051 | 0.988 |
| 2 | 1875 | 0.031 | 0.969 |
| 2.25 | 732 | 0.012 | 0.982 |
| 2.5 | 421 | 0.007 | 0.989 |
| 2.75 | 293 | 0.005 | 0.994 |
| 3 | 263 | 0.004 | 0.998 |
| 3.25 | 121 | 0.002 | 1 |
| TOTAL | 59937 | | |

STATISTICAL MAXIMUM TIME PERIOD: 3 DAYS
STATISTICAL MINIMUM TIME PERIOD: 0.75 DAY

In the example of blood sugar level, shown in Table 1, the cumulative relative frequency exceeds 0.98 at about 5 weeks. Therefore, a 98% interval, which is standard examination intervals I, is 1 to 5 weeks. Further, in the example of body temperature, shown in Table 2, the cumulative relative frequency exceeds 0.98 at about 2.25 days. Therefore, a 98% interval, which is standard examination intervals I, is 0.75 to 2.25 days. Further, in the examples shown in Table 1 and Table 2, determined minimum standard examination interval $I_{min}$ and maximum standard interval $I_{max}$ are indicated by bold numbers.

In the above descriptions, the method for determining standard examination intervals based on a frequency distribution was explained. Next, a case of obtaining standard examination intervals I by using standard deviation will be described, assuming that the distribution of examination intervals of examination data in the past is similar to a normal distribution.

Plural examination intervals of examination Ti are obtained for each examination item i (S1). Average $\mu$ and variance $\sigma^2$ of examination intervals of examination Ti are obtained based on the obtained examination intervals of examination Ti (S2). Examination intervals belonging to an interval of 98% of a normal distribution are standard examination intervals I, and the interval of 98% is in the range of about 2.05*$\sigma$ (standard deviation). Therefore, $$\mu - 2.05 \times \sigma \leq \text{Standard Examination Intervals} \leq \mu + 2.05 \times \sigma.$$

Further, minimum standard examination interval $I_{min}$ among standard examination intervals is:

$$I_{min} = \mu - 2.05 \times \sigma \quad (1).$$

Further, maximum standard examination interval $I_{max}$ among standard examination intervals is:

$$I_{max} = \mu + 2.05 \times \sigma \quad (2) \, (S3).$$

Obtained standard examination intervals I for each examination item i are stored in the clinical information database 32.

In the above descriptions, calculation was performed by assuming that examination intervals follow a normal distribution. However, the examination intervals do not always follow a normal distribution. In some actual cases, a 98% interval obtained by using a normal distribution and a 98% interval obtained by using cumulative frequency differ from each other. Therefore, standard examination intervals appropriately adjusted, based on experiences, within predetermined ranges from the minimum value and the maximum value of the 98% interval obtained in a normal distribution may be determined, as the minimum standard examination interval and the maximum standard examination interval. For example, the number of days and the number of weeks that are round numbers may be determined as the examination intervals.

In the above descriptions, the distribution of examination intervals was assumed to follow a normal distribution. More accurately, it is desirable to use a gamma distribution or the like.

In the above descriptions, a case in which standard examination intervals I are determined not according to a disease but based on examination intervals for an examination item was described. However, examination intervals for the same examination item are different depending on a disease in some cases. Therefore, standard examination intervals I may be determined by collecting statistics of each examination item for each disease.

Next, a flow of processing for displaying graphs at the clinical department terminal will be described with reference to FIG. 1 and FIG. 2B. A doctor in a clinical department inputs a patient ID into an input box displayed on a display screen of a display device at the clinical department terminal 2 to check clinical information S about a patient to be diagnosed (S10). The input patient ID is received by the patient specification receipt means 21, and a clinical information integrated viewer for the patient is displayed on the display screen. The clinical information obtainment means 22 obtains, based on the received patient ID, clinical information S corresponding to the patient ID from the clinical information database 32 in the clinical information management server 3, and stores clinical information S in a memory of the clinical department terminal 2 (S11). Further, the clinical information obtainment means 22 obtains a disease name of the patient from an electronic chart included in obtained clinical information S.

The display mode determination means 23 extracts, based on graph generation information corresponding to the disease of the patient, examination data for plural examination items i corresponding to the disease, which are set in the graph generation information, from obtained clinical information S about the patient to be diagnosed. Further, the display mode determination means 23 obtains standard examination intervals I corresponding to each of plural examination items i from the clinical information database 32 in the clinical information management server 3 (S12).

The graph display means 24 determines a display range of the horizontal axis and the vertical axis of a graph and scales on each of the axes. The display period is a whole time period in which examination data for any one of the examination items about the patient are present (S13). The horizontal axis is a time axis. Scales on the vertical axis of the graph are assigned based on the range of possible examination values of examination data for each examination item i displayed by the graph. Since the range of possible examination values differs in each examination item i, scales on the vertical axis are different in each examination item i. Further, the scales on the vertical axis are assigned in such a manner that line graphs of examination items do not overlap with each other (S14). Alternatively, a doctor may input a display period of graphs at the input device, and the display period of the horizontal axis of graphs may be determined based on the input display period.

Next, the display mode determination means 23 determines whether a line graph should be displayed in an ordinary display mode or a low visual recognizability display mode by comparing a display period of the time axis and standard examination intervals I of each examination item i (S15). The low visual recognizability display mode may be a simple display mode in which display simpler than an ordinary display mode is performed or non-display.

As described above, a color, a line type, marks (marks indicating positions of data points representing examination data, such as ● and ■) and the like constituting a line graph have been determined in advance for each examination item i. In a line graph displayed in a simple display mode, a part of elements, such as a line color and marks, constituting the line graph is the same as a line graph displayed in an ordinary mode so that the line graphs are related to each other, but a part of the elements is omitted or varied. The part of elements to be varied or omitted is determined based on a predetermined rule. For example, in a simple display mode, the size of a mark indicating the position of a data point representing examination data is reduced, compared with an ordinary display mode. Alternatively, in the simple display mode, no mark indicating the position of each data point representing examination data is displayed, but only a line is displayed, or in the simple display mode, the width of a line is reduced, compared with the ordinary display mode. Alternatively, different line types are adopted. If a solid line is used for the ordinary display mode, a less noticeable line, such as a broken line, is used for the simple display mode. Alternatively, a less noticeable color is used for a line in the simple display mode, compared with a line in the ordinary display mode, or data points are not connected to each other in the simple display mode. When the color is changed to a less noticeable color, it is desirable that a range of colors recognizable by humans as the same color is defined in a color space so that a relationship between a line graph in the ordinary display mode and a line graph in the simple display mode for the same examination item is recognizable. It is desirable that a color that gives a sense of high visual recognizability and a color that gives a sense of low visual recognizability are determined in advance by changing the brightness and the saturation in the range, and that the determined colors are used in the ordinary display mode and in the simple display mode.

When there are examinations at a short examination interval, such as vital examination, which are performed many times a day, and examinations at a long examination interval, which are performed every few days or every few weeks, among examinations, the whole time period in which some examination data are present is often a period of several months. The examination at the short examination interval, such as vital examination, is performed in a display period, such as a time period while a patient is hospitalized. In the interval, the number of pieces of examination data is extremely large, and changes in a line graph are dense. When a change in examination data at a long examination interval is observed, examination data at such an extremely short examination interval interfere with observation of examination data at the long examination interval. Therefore, a change in examination data at the long examination interval becomes easily observable by displaying a line graph for examination item i of an extremely short examination interval in a simple display mode.

Judgment as to whether a line graph for examination item i of a short examination interval should be displayed in a simple display mode or not is made by comparing a display period and standard examination intervals I for each examination item. A line graph for examination item i in which the number of pieces of examination data having probabilities of presence in the display period is less than equal to the first threshold is displayed in the ordinary display mode. A line graph for examination item i in which the number of pieces of examination data having probabilities of presence in the display period is greater than the first threshold is displayed in the simple display mode.

The graph display means 24 generates a line graph in a display mode determined for each examination item i (S16), and displays all of the line graphs on the same coordinates (S17).

Figure 5:
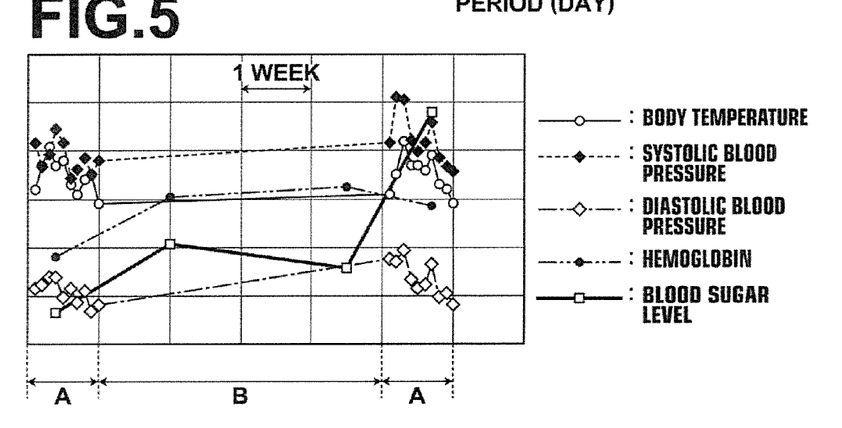
FIG. 5 is an example of line graphs in which all data points representing examination data are connected by lines.
Figure 6:
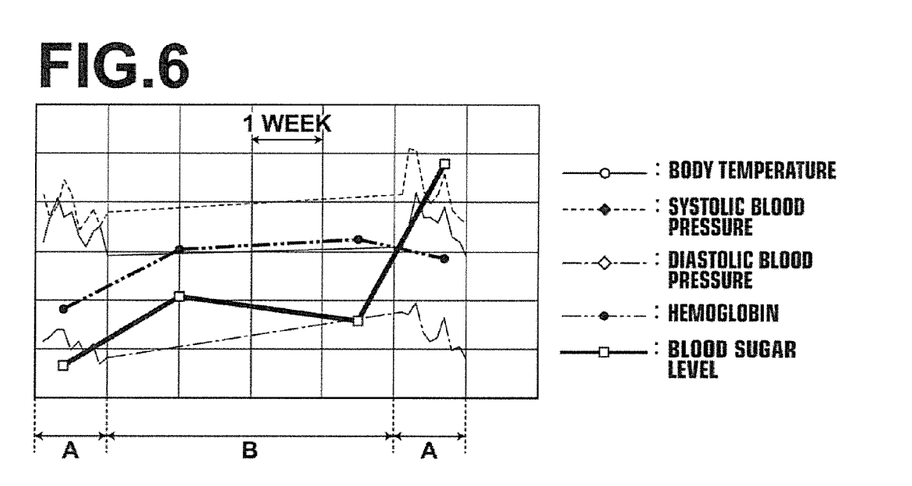
FIG. 6 is an example of line graphs in which a simple display mode is adopted for examination items of short examination intervals and an ordinary display mode is adopted for examination items of long examination intervals.
Figure 7:
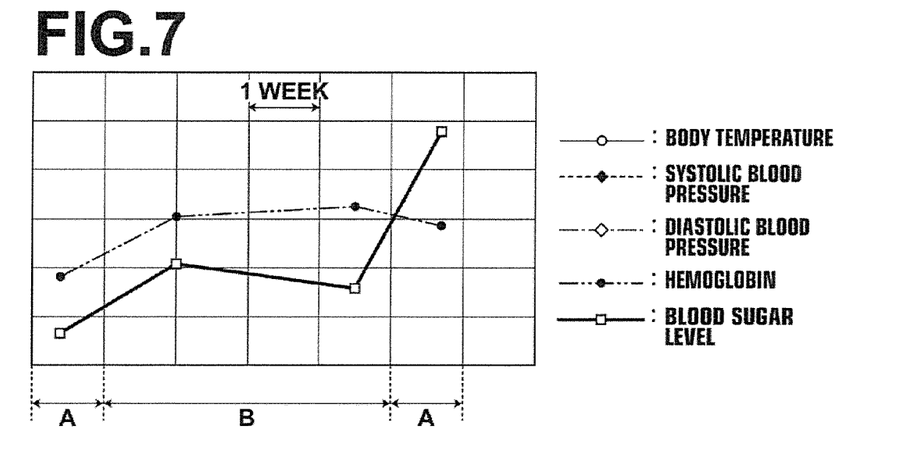
FIG. 7 is an example of line graphs in which examination items of short examination intervals are not displayed, but examination items of long examination intervals are displayed.
Figure 8:
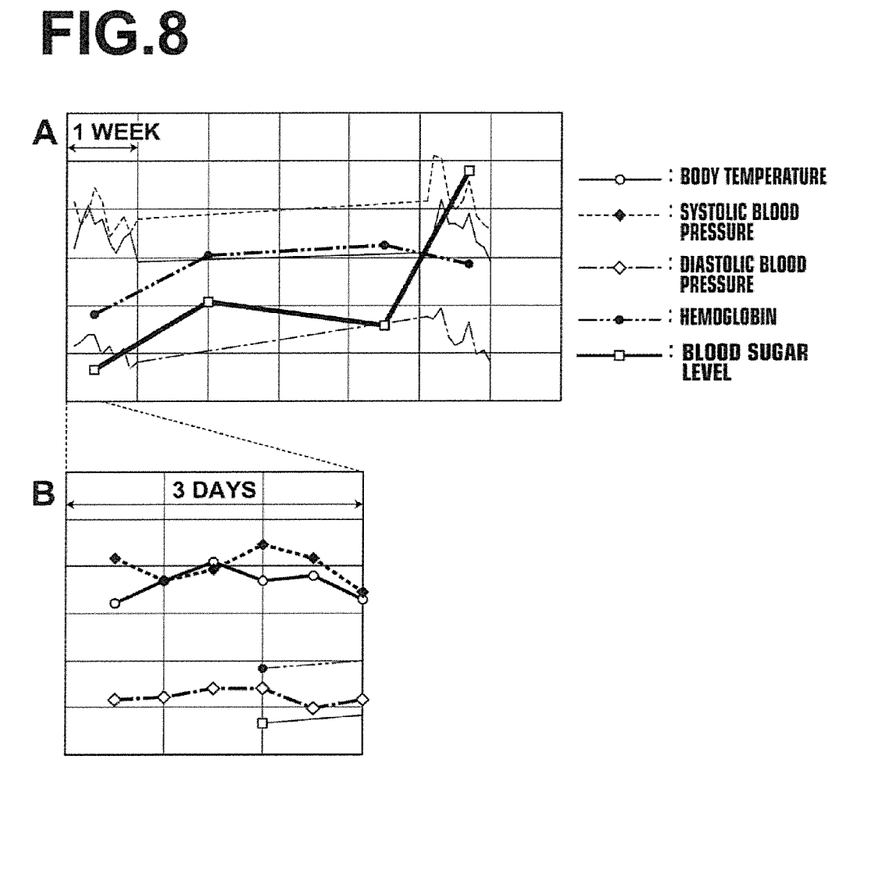
FIG. 8 is an example of line graphs in which an ordinary display mode is adopted for examination items of short examination intervals and a simple display mode is adopted for examination items of long examination intervals by switching display periods.

Next, specific examples of line graphs will be described with reference to Table 1, Table 2 and FIG. 5 through FIG. 8. FIG. 5 illustrates an example in which all data points representing examination data for examination items i are connected by lines. In the line graphs, a solid line represents body temperature, a broken line represents systolic blood pressure, a dot dashed line represents diastolic blood pressure, two-dot dashed line represents hemoglobin, and a bold line represents blood sugar level. In FIG. 5 through FIG. 7 and FIG. 8, Section A, a square box on the horizontal axis represents one week. In FIG. 8, Section B, a square box on the horizontal axis represents one day. In FIG. 5 and FIG. 6, a patient is hospitalized in time periods A. Therefore, vital (body temperature and blood pressure) data are present in the time period. Examinations for hemoglobin and blood sugar level are regularly performed in the whole time period of A and B, regardless of whether the patient is hospitalized.

Specifically, it is desirable that judgment as to whether a line graph for examination item i of a short examination interval should be displayed in a simple display mode or not is made by determining the display mode based on maximum standard examination interval $I_{max}$, which is the maximum interval in the range of standard examination intervals I, for each examination item i. For example, when a display period exceeds a time period that is 15 times as long as maximum standard examination interval $I_{max}$, there is a probability of presence of at least 15 pieces of examination data in the display period, and the line graph becomes extremely dense. Therefore, 15 is used as the first threshold, and examination item i in which the period of maximum standard examination interval $I_{max} \times 15$ exceeds the display period is displayed in a simple display mode. Meanwhile, examination item i in which the period of maximum standard examination interval $I_{max} \times 15$ is less than or equal to the display period is displayed in an ordinary display mode.

In the case of blood sugar level, shown in Table 1, maximum standard examination interval $I_{max}$ is 5 weeks. Therefore, 5 weeks×15=75 weeks, and a simple display mode is not adopted in a display period in the range of about 1 year. Meanwhile, in the case of body temperature, shown in Table 2, maximum standard examination interval $I_{max}$ is 2.25 days. Therefore, when a display interval is longer than or equal to 2.25 days×15=33 day, a simple display mode is adopted. If the display period is 1 year, display in the simple display mode is performed. FIG. 6 is an example of line graphs in which a simple display mode is adopted for vital data, such as body temperature, systolic blood pressure and diastolic blood pressure, and an ordinary display mode is adopted for hemoglobin and blood sugar level.

Alternatively, instead of switching the display mode between the ordinary display mode and the simple display mode, a line graph or graphs for only examination item or items i in which the number of pieces of examination data having probabilities of presence in the display period has been judged to be less than or equal to the first threshold may be displayed, and no line graph for examination item or items i in which the number of pieces of examination data having probabilities of presence in the display period has been judged to be greater than the first threshold may be displayed by comparing the display period and standard examination intervals I for each examination item. FIG. 7 is an example in which no line graph of vital data, such as body temperature, systolic blood pressure and diastolic blood pressure, is displayed and line graphs of hemoglobin and blood sugar level are displayed.

As a display mode in which a line graph for examination item i at a short examination interval is displayed in a simple display mode, a part of elements constituting a line graph may be omitted or varied as described above. Alternatively, the line graph may be displayed by performing thinning on the examination data, or the display period may be divided into short time periods, and an average for each unit of short time period may be displayed, or only a maximum value and/or a minimum value in each unit of short time period may be displayed.

Meanwhile, when a user wants to observe a line graph for examination item i of a short examination interval, the display period switching receipt means 25 enlarges and displays only 3 days in first period A (please refer to FIG. 8, S18-YES). Then, the display period becomes 3 days, and the scale on the horizontal axis in the coordinates changes (S14).

When enlarged display is performed, only one data point representing examination data for examination item i of a long examination interval may be present in the display period in some cases, or no data point representing examination data may be present, and only a line may be displayed in some cases. When a change in examination data at a short examination interval is observed, such a line interferes with observation of a change in examination data at the short examination interval. Therefore, the display period of coordinates displayed on a display screen and standard examination intervals I for each examination item i are compared with each other, and whether a line graph for the examination item i should be displayed in an ordinary display mode or a simple display mode, which is a less noticeable mode, is determined.

Judgment as to whether a line graph for examination item i of a long examination interval should be displayed in a simple display mode or not is made by comparing the display period and standard examination intervals I for each examination item. A line graph for an examination item in which the number of pieces of examination data having probabilities of presence in the display period has been judged to be greater than or equal to a second threshold (for example, 2 pieces) is displayed in an ordinary display mode, and a line graph for an examination item in which the number of pieces of present examination data has been judged to be less than the second threshold is displayed in a simple display mode (S15).

The graph display means 24 generates a line graph for each examination item i according to the determined display mode (S16), and displays the line graphs for all of examination items i on the same coordinates (S17).

Specifically, in the method for judging whether a line graph for examination item i of a long examination interval should be displayed in a simple display mode or not, it is desirable to determine a display mode based on minimum standard examination interval $I_{min}$, which is the minimum interval in the range of standard examination intervals I, for each examination item i. For example, when a display period exceeds a time period that is ½ times as long as minimum standard examination interval $I_{min}$, there is a probability of presence of two or less pieces of examination data in the display period, and only a line of the line graph is displayed. Therefore, "2" is used as the second threshold, and examination item i in which a period of minimum standard examination interval $I_{min} \times ½$ exceeds the display period is displayed in a simple display mode. Meanwhile, examination item i in which a period maximum standard examination interval $I_{max} \times ½$ is less than or equal to the display period is displayed in an ordinary display mode.

In the case of blood sugar level, shown in Table 1, minimum standard examination interval $I_{min}$ is 1 week. Therefore, 1 week×½=3.5 days, and a simple display mode is adopted in a three day display mode. Meanwhile, in the case of body temperature, shown in Table 2, minimum standard examination interval $I_{min}$ is 0.75 day. Therefore, 0.75×½≈0.38 day, and an ordinary display mode is adopted in the three day display mode. FIG. 8, Section B is an example of line graphs in which an ordinary display mode is adopted for vital data, such as body temperature, systolic blood pressure and diastolic blood pressure, and a simple display mode is adopted for hemoglobin and blood sugar level.

FIG. 8 is an example of line graphs in which display in an ordinary display mode and display in a simple display mode are performed. Alternatively, vital data, such as body temperature, systolic blood pressure and diastolic blood pressure, may be displayed, and no examination data for hemoglobin and blood sugar level may be displayed.

When the display period switching receipt means 25 has switched the display period again to the whole time period in which examination data are present, display is switched to the display illustrated in FIG. 8, Section A (S18-YES). After then, a display period and standard examination intervals I are compared with each other again, and a display mode of a line graph for each examination item i is determined, and line graphs are displayed (S14 through S17).

In the above descriptions, whether a display period is compared with maximum standard examination interval $I_{max}$ or minimum standard examination interval $I_{min}$ of standard examination intervals I is changed based on whether a line graph for examination item i of a short examination interval should be displayed in a simple display mode or a line graph for examination item i of a long examination interval should be displayed in a simple display mode. Alternatively, one of standard examination intervals I, for example, such as an average or a median, may be compared with the display period, and a threshold may be determined.

Further, in the above descriptions, judgment is made by using different standard examination intervals I (maximum standard examination interval $I_{max}$ and minimum standard examination interval $I_{min}$) for a case of judging whether a line graph for examination item i of a short examination interval should be displayed in a simple display mode and a case of judging whether a line graph for examination item i of a long examination interval should be displayed in a simple display mode. For example, an average or a median of examination intervals may be used as one of standard examination intervals I, and a display period and the one of standard examination intervals I may be compared with each other. When the number of pieces of examination data having probabilities of existence in the display period is within a range from the first threshold to the second threshold, the ordinary display mode may be adopted as the display mode of a line graph for examination item i. When the number of pieces of examination data having probabilities of existence in the display period is greater than the first threshold or less than the second threshold, the simple display mode may be adopted as the display mode of a line graph for examination item.

Through such processing, for example, when a first threshold is 25 and a second threshold is 2, if there is a probability that 25 through 2 pieces of examination data are present in the display period, it is possible to display a line graph in the ordinary display mode. Regarding examination item i in which the number of piece of examination data is one or less, and only a line is displayed, and examination item i in which the number of pieces of examination data is greater than 25, and the examination data densely change, it is possible to display line graphs in a simple display mode.

In the above descriptions, an example in which judgment is made based on the ratio of the standard examination interval to the display period was described. Since a display period in which data points are displayable differs depending on the width of a display of the clinical department terminal 2, or the like. Therefore, it is desirable to determine a display mode based on a time period indicated by a division of scale in a reference display period.

Further, in the above descriptions, a case in which standard examination intervals I are obtained from the clinical information database 32 was described. Alternatively, standard examination intervals I corresponding to each examination item may be stored in advance in the clinical information integrated display viewer.

The present disclosure is not limited to embodiments of the present disclosure. A part or all of composition elements of the graph generation apparatus may be configured by a workstation, or by at least one workstation, a server and a storage unit connected to each other through a network. Here, each equipment is controlled by a program for generating a graph as described in the specification of the present application, and which is installed from a recording medium, such as a CD-ROM. The program may be installed after being downloaded from a storage unit of a server connected through a network, such as the Internet.

What is claimed is:

1. A graph display apparatus that displays, on coordinates having a horizontal axis and a vertical axis, one of which is a time axis and the other one is an axis of examination values, line graphs connecting data points representing examination data about a patient by lines in order of time of examination for a plurality of examination items, the apparatus comprising:
   a processor configured to,
      obtain the number of pieces of examination data having probabilities of presence in a display period of the time axis by comparing a standard examination interval, which is a standard interval at which examination of each of the plurality of examination items is performed, and the display period, and determine, based on whether the obtained number of pieces of examination data is greater than or equal to a threshold, an ordinary display mode or a low visual recognizability display mode, in which visual recognizability is low, as a display mode of a line graph for each of the plurality of examination items, and
      generate the line graphs of examination data for the plurality of examination items according to the display mode that has been determined for each of the plurality of examination items, and display the line graphs on the coordinates.

2. The graph display apparatus, as defined in claim 1, wherein the processor compares the display period and the standard examination interval of each of the plurality of examination items, and determines the ordinary display mode, as the display mode of a line graph for an examination item in which the number of pieces of examination data having probabilities of presence in the display period has been judged to be less than or equal to a first threshold, and determines the low visual recognizability display mode, as the display mode of a line graph for an examination item in which the number of pieces of examination data having probabilities of presence in the display period has been judged to be greater than the first threshold.

3. The graph display apparatus, as defined in claim 2, wherein the processor further configured to
   receive switching to display in which display in a part of the display period is enlarged,
   wherein when switching to the display has been received, the processor compares the part of the display period and the standard examination interval of each of the plurality of examination items, and determines the ordinary display mode, as the display mode of a line graph for an examination item in which the number of pieces of examination data having probabilities of presence in the part of the display period is greater than or equal to a second threshold, and determines the low visual recognizability display mode, as the display mode of a line graph for an examination item in which the number of pieces of examination data having probabilities of presence in the part of the display period is less than the second threshold.

4. The graph display apparatus, as defined in claim 1, wherein the processor compares the display period and the standard examination interval of each of the plurality of examination items, and determines the ordinary display mode, as the display mode of a line graph for an examination item in which the number of pieces of examination data having probabilities of presence in the display period has been judged to be greater than or equal to a second threshold, and determines the low visual recognizability display mode, as the display mode of a line graph for an examination item in which the number of pieces of examination data having probabilities of presence in the display period has been judged to be less than the second threshold.

5. The display apparatus, as defined in claim 1, wherein the processor further configured to
obtains for each of the plurality of examination items, examination intervals between examinations performed on a plurality of patients, and determine a predetermined examination interval among examination intervals within a predetermined range from an average or a median of the examination intervals at which examination for each of the plurality of examination items has been performed, as the standard examination interval.

6. The graph display apparatus, as defined in claim 1, wherein the standard examination interval is determined based on a disease.

7. The graph display apparatus, as defined in claim 1, wherein the line graph displayed in the ordinary display mode connects data points representing examination data, and the line graph displayed in the low visual recognizability display mode does not connect data points representing examination data, but displays only a mark indicating a position of each of the data points representing examination data.

8. The graph display apparatus, as defined in claim 1, wherein the line graph displayed in the ordinary display mode connects data points representing examination data and also displays a mark indicating a position of each of the data points, and the line graph displayed in the low visual recognizability display mode does not display any mark indicating a position of each of the data points, but only connects data points representing examination data.

9. An operation method of a graph display apparatus that displays, on coordinates having a horizontal axis and a vertical axis, one of which is a time axis and the other one is an axis of examination values, line graphs connecting data points representing examination data about a patient by lines in order of time of examination for a plurality of examination items, the method comprising:
a display mode determination step in which a processor configured to obtain the number of pieces of examination data having probabilities of presence in a display period of the time axis by comparing a standard examination interval, which is a standard interval at which examination of each of the plurality of examination items is performed, and the display period, and determine, based on whether the obtained number of pieces of examination data is greater than or equal to a threshold, an ordinary display mode or a low visual recognizability display mode, in which visual recognizability is low, as a display mode of a line graph for each of the plurality of examination items; and
a graph display step in which the processor configured to generate the line graphs of examination data for the plurality of examination items according to the display mode that has been determined for each of the plurality of examination items, and display the line graphs on the coordinates.

10. A non-transitory recording medium having stored therein a graph display program that causes a computer of a graph display apparatus that displays, on coordinates having a horizontal axis and a vertical axis, one of which is a time axis and the other one is an axis of examination values, line graphs connecting data points representing examination data about a patient by lines in order of time of examination for a plurality of examination items to function as:
the graph display program executed by a processor of the computer that obtains the number of pieces of examination data having probabilities of presence in a display period of the time axis by comparing a standard examination interval, which is a standard interval at which examination of each of the plurality of examination items is performed, and the display period, and determines, based on whether the obtained number of pieces of examination data is greater than or equal to a threshold, an ordinary display mode or a low visual recognizability display mode, in which visual recognizability is low, as a display mode of a line graph for each of the plurality of examination items; and
the graph display program executed by the processor of the computer that generates the line graphs of examination data for the plurality of examination items according to the display mode that has been determined for each of the plurality of examination items, and displays the line graphs on the coordinates.

* * * * *